Oct. 8, 1957 H. C. SWIM Plant Pat. 1,651
APRICOT TREE
Filed Nov. 6, 1956
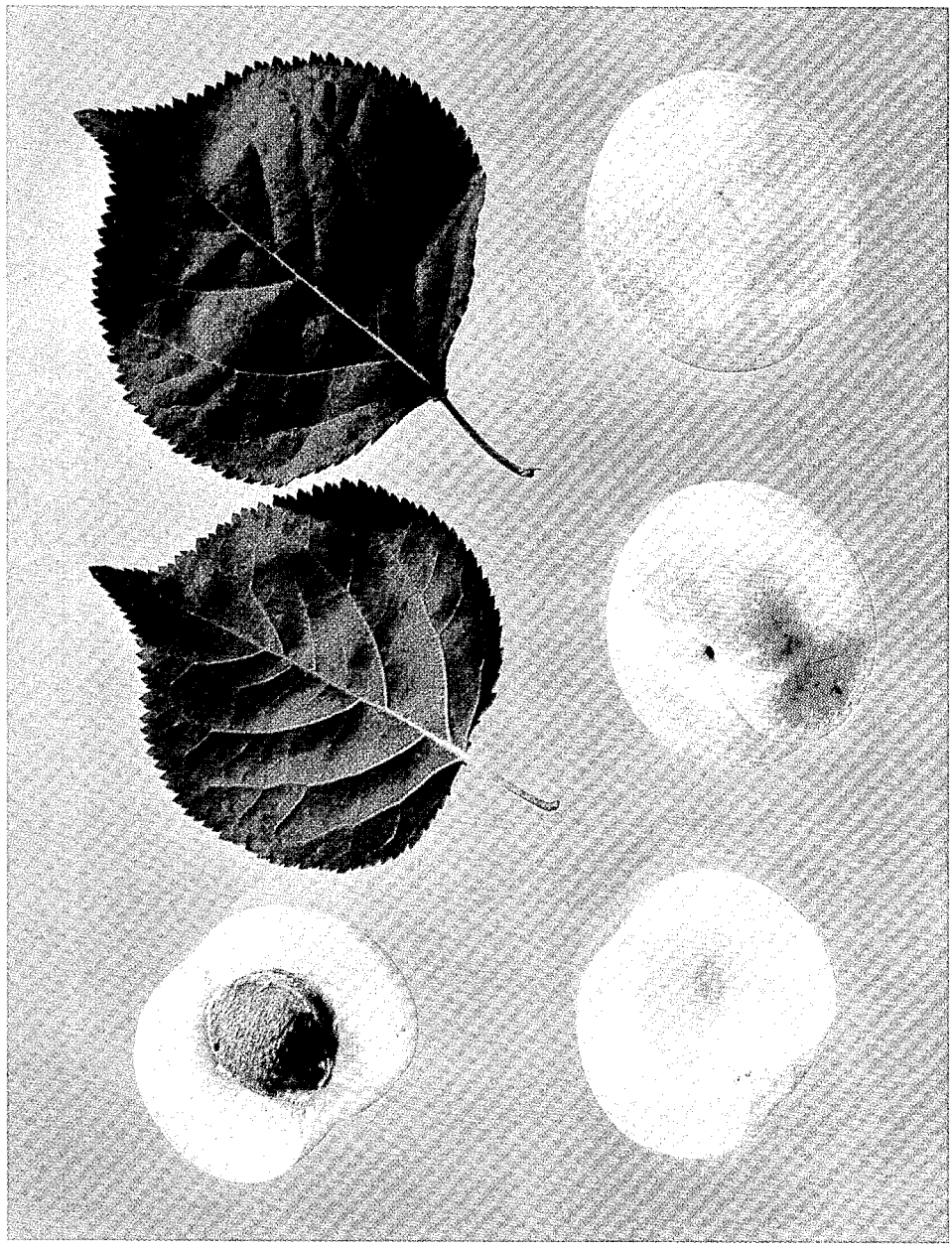
Inventor.
H. C. Swim
By: Robb & Robb
Attorneys.

United States Patent Office

Plant Pat. 1,651
Patented Oct. 8, 1957

1,651

APRICOT TREE

Herbert C. Swim, Ontario, Calif., assignor to Armstrong Nurseries, Inc., Ontario, Calif., a corporation of California Application November 6, 1956, Serial No. 620,780

1 Claim. (Cl. 47—62)

The present invention relates to a new and distinct variety of apricot tree which was originated by me by crossing an unnamed and unpatented, early-blooming sport of "Royal" apricot (unpatented) with the unpatented variety "Casaba," the unnamed sport being the seed parent, and the "Casaba" variety being the pollen parent.

The primary objective of this breeding was to produce a new and improved apricot variety which combines the best characteristics of the two parent varieties. This objective was fully achieved, as evidenced by the following unique combination of features which are outstanding in the new variety:

(1) The medium to large size of the fruit;

(2) A high degree of desirable red skin color on the side of the fruit which is exposed to the sun;

(3) A slightly higher winter chilling requirement than that of the "Royal" apricot, with a consequent blooming of some 3 to 10 days later than "Royal" in southern California; and (4) A fruit maturation period from peak bloom to tree ripe from approximately 10 days to 2 weeks shorter than that of "Royal" apricot, and a ripening period of from one to 2 weeks ahead of "Royal" in southern California, occurring in late June.

In comparison with its seed parent, my new variety bears somewhat larger fruit; has a higher degree of red skin coloring (this parent having little or no red color); a higher winter chilling requirement and a resulting later blooming period; and a more uniform distribution of the fruit on the tree (the parent usually producing a large portion of its fruit near the terminals of its long and more or less willowy branches).

As compared with its pollen parent, "Casaba," my new variety has a much lower winter chilling requirement than this parent which has a chilling requirement too high for southern California; and has more skin color than the fruit of this parent as grown in northern California.

The foregoing characteristics and distinctions definitely differentiate my new variety from its parents, as well as from all other varieties of which I am aware, and asexual reproduction of the new variety by grafting, as performed at Ontario, California, shows that said characteristics come true to form and are established and transmitted through succeeding propagations.

The accompanying drawing shows typical specimens of the foilage and fruit of my new variety, with both the upper and lower surfaces of the foilage being illustrated and both exterior and sectional views of the fruit being shown, all as being depicted in color as nearly true as it is reasonably possible to make the same in a color illustration of this character.

The following is a detailed description of my new variety, as based upon observations of specimens grown at Ontario, California, with color terminology in accordance with Robert F. Wilson's Horticultural Colour Chart, except where color terminology is given from Ridgway's Color Standards and Nomenclature (hereinafter abbreviated as "Ridgway"), or where general color terms of ordinary dictionary significance are obvious:

Dates of first and last picking: Generally ripens in late June, although over prolonged observations, dates of first ripening varied from June 18 to July 3, with ripening ending from June 27 to July 10.

Tree: From large to medium size; vigorous; upright; dense; vase-formed; very productive; regular bearer.

*Trunk.*—From stocky to medium caliper in relation to length; from medium to shaggy in surface roughness.

*Branches.*—From stocky to medium caliper in relation to length; from smooth to medium roughness; dull. Color—near Deep Brownish Drab, Plate XLV (Ridgway), overlaid with between Pale Mouse Gray, Plate LI (Ridgway) and Light Mouse Gray, Plate LI (Ridgway). Lenticels—few; medium size.

*Leaves.*—From very broadly ovate to orbicular; abruptly pointed; mucronate; from thick to medium thickness; relatively smooth. Size—large; length—from 3 inches to 3½ inches; width—from 2¾ inches to 3¼ inches. Color: upper surface—between Cress Green, Plate XXXI (Ridgway) and Dark Dull Yellow-Green, Plate XXXII (Ridgway); under surface—between Chromium Green, Plate XXXII (Ridgway) and Deep Dull Yellow-Green (1), Plate XXXII (Ridgway). Margin—coarsely serrate. Petiole—from long to medium length; from 1 inch to 1¼ inches in length; medium thickness. Glands—average 2 or 3 in number; alternate; medium size; globose; positioned on petiole below attachment of leaf blade; color—green. Stipules—very short; broad.

Flower buds: Medium size; from medium to short length; plump; glabrous.

Flowers:

*Dates first and full bloom.*—Over prolonged period of observations, dates varied from February 18 to March 8 and from March 3 to March 24, respectively, due to weather variations from year-to-year; medium earliness as compared with other varieties.

*Size.*—Medium.

*Color.*—White.

Fruit:

*Maturity when described.*—Eating-ripe. Date—June 24.

*Size.*—Only slightly variable; large. Axial diameter—from 1⅝ inches to 1¾ inches. Transverse diameter in suture plane—from 1¾ inches to 1⅞ inches. Diameter at right angles to suture plane—from 1⅝ inches to 1¾ inches.

*Form.*—Slightly variable; symmetrical; globose; at times somewhat compressed laterally toward suture.

*Suture.*—Shallow; extends from base to apex, but discontinuous at apex.

*Ventral surface.*—Rounded slightly; usually strongly lipped toward base, approximately ¼ to ½ the distance from base toward apex on both sides; lips usually equal.

*Cavity.*—From rounded to somewhat elongated in suture plane, with suture showing on one side. Depth—from about ⅛ inch to 3/16 inch. Breadth—about ¼ inch.

*Base.*—Rounded.

*Apex.*—Rounded and slightly depressed; with pistil point slightly depressed.

*Stem.*—From ¼ inch to 5/16 inch in length; medium caliper; pubescent; medium adherence to stone.

*Skin.*—Thin; tender; tenacious to flesh; slight tendency to crack. Color—between Tangerine Orange, Plate 9/1, page 9 and Orpiment Orange, Plate 10/2, page 10, blushed on side exposed to sun with between Scarlet, Plate 19/2, page 19 and Geranium Lake, Plate 20/1, page 20. Down—scant; very short; does not roll up when rubbed.

*Flesh.*—Color—between Orpiment Orange, Plate 10/1, page 10 and Marigold Orange, Plate 11/1, page 11. Surface of pit cavity—color—near Marigold Orange, Plate 11/1, page 11. Amygdalin—scant. Juice—from abundant to moderate; rich. Texture—medium firmness; fine; melting. Fibres—medium size; tender. Ripens—fairly evenly; slightly earlier at apex. Flavor—mild; delicate. Aroma—not pronounced. Eating quality—good.

Stone: Free; adheres to flesh somewhat along ventral edge; fibres of medium length; free on sides; parts from flesh smoothly.

*Size.*—Medium. Length—from ⅞ inch to 1 inch. Breadth—from ⅝ inch to ¾ inch. Thickness—½ inch.

*Form.*—Ovoid; very slightly cuneate toward apex.

*Base.*—Straight.

*Hilum.*—Oval.

*Apex.*—Nearly rounded.

*Sides.*—Generally equal; curved on right and left sides.

*Surface.*—Regularly pitted only slightly throughout.

*Ridges.*—Sharp ridges only along ventral edge.

*Pits.*—Slightly elongated.

*Ventral edge.*—Thick; with wing usually extending ½ distance from apex toward base.

*Dorsal edge.*—Full; with no groove; no ridges on either side.

*Tendency to split.*—Very slight.

*Color.*—Between Verona Brown, Plate XXIX (Ridgway) and Snuff Brown, Plate XXIX (Ridgway).

Use: Market; local; dessert.

Keeping quality: Medium.

Shipping quality: Medium.

I claim:

A new and distinct variety of apricot tree, substantially as herein shown and described, chararcterized particularly as to novelty by its medium to large fruit, the relatively high red skin color on the side of the fruit exposed to the sun, its slightly higher winter chilling requirement than that of "Royal" apricot (unpatented), its habit of blooming from 3 to 10 days later than "Royal" apricot in southern California, its shorter maturation period than "Royal" apricot, and its earlier ripening habit ranging from one to two weeks ahead of "Royal" apricot in southern California.

No references cited.